(12) United States Patent
Krishnan et al.

(10) Patent No.: US 9,211,419 B2
(45) Date of Patent: Dec. 15, 2015

(54) TREATMENTS OF DISEASE OR DISORDERS USING NANOPARTICLES FOR FOCUSED HYPERTHERMIA TO INCREASE THERAPY EFFICACY

(71) Applicants: Sunil Krishnan, Houston, TX (US); Parmeswaran Diagaradjane, Houston, TX (US); Jon Alexander Schwartz, Sugar Land, TX (US); James Chunjay Wang, Arlington, TX (US)

(72) Inventors: Sunil Krishnan, Houston, TX (US); Parmeswaran Diagaradjane, Houston, TX (US); Jon Alexander Schwartz, Sugar Land, TX (US); James Chunjay Wang, Arlington, TX (US)

(73) Assignees: Nanospectra Biosciences, Inc., Houston, TX (US); Board of Regents, The University of Texas System, Austin, TX (US)

( * ) Notice: Subject to any disclaimer, the term of this patent is extended or adjusted under 35 U.S.C. 154(b) by 14 days.

(21) Appl. No.: 13/742,446

(22) Filed: Jan. 16, 2013

(65) Prior Publication Data
US 2013/0197295 A1    Aug. 1, 2013

Related U.S. Application Data

(63) Continuation of application No. 12/863,163, filed as application No. PCT/US2009/000315 on Jan. 16, 2009, now abandoned.

(60) Provisional application No. 61/011,266, filed on Jan. 16, 2008.

(51) Int. Cl.
| A61N 2/00 | (2006.01) |
|---|---|
| A61N 5/10 | (2006.01) |
| A61K 41/00 | (2006.01) |
| A61K 47/48 | (2006.01) |
| A61N 1/40 | (2006.01) |
| A61N 5/06 | (2006.01) |
| A61N 7/00 | (2006.01) |
| A61N 5/067 | (2006.01) |

(52) U.S. Cl.
CPC ............ *A61N 2/002* (2013.01); *A61K 41/0052* (2013.01); *A61K 47/48215* (2013.01); *A61N 1/406* (2013.01); *A61N 5/0625* (2013.01); *A61N 5/1077* (2013.01); *A61N 5/062* (2013.01); *A61N 7/00* (2013.01); *A61N 2005/067* (2013.01); *A61N 2005/0659* (2013.01); *A61N 2005/1088* (2013.01); *A61N 2005/1098* (2013.01)

(58) Field of Classification Search
CPC ...................................................... A61N 2/002
See application file for complete search history.

(56) References Cited

U.S. PATENT DOCUMENTS

| 4,569,836 | A |  | 2/1986 | Gordon |
|---|---|---|---|---|
| 5,236,410 | A |  | 8/1993 | Granov et al. |
| 5,620,479 | A |  | 4/1997 | Diederich |
| 6,165,440 | A | * | 12/2000 | Esenaliev ..................... 424/1.11 |
| 6,344,272 | B1 |  | 2/2002 | Oldenburg et al. |
| 6,685,986 | B2 |  | 2/2004 | Oldenburg et al. |
| 6,957,108 | B2 |  | 10/2005 | Turner et al. |
| 7,367,934 | B2 |  | 5/2008 | Hainfeld et al. |
| 2005/0090732 | A1 | * | 4/2005 | Ivkov et al. ................... 600/411 |

FOREIGN PATENT DOCUMENTS

| EP | 0913167 B1 | 5/1999 |
|---|---|---|
| WO | 00/52714 A1 | 9/2000 |
| WO | 2005/110261 A2 | 11/2005 |
| WO | 2006/099413 A2 | 9/2006 |
| WO | 2008152411 A1 | 12/2008 |

OTHER PUBLICATIONS

Ji et al (J. Phys. Chem. 2007; 111: 6245-6251).*
Welsh et al (Mol. Cancer Ther. 2003; 2: 235-243).*
Pawelek et al (Lancet Oncol. 2003; 4:548-56).*
Bushberg et al. ((2002). Chapter 2: Radiation and The Atom. in the essential physics of medical imaging; second edition, Lippincott Williams & Wilkins).*
European Patent Office; Office Action; European Application No. 09 702 553.0; Mar. 28, 2013.
Welsh, S.J., et al; The Thioredoxin Redox Inhibitors 1-Methylpropyl 2-Imidazolyl Disulfide and Pleurotin Inhibit Hypdxia-Induced Factor 1 and Vascular Endothelial Growth Factor Formation; Molecular Cancer Therapeutics, vol. 2, pp. 235-243, Mar. 2003.

(Continued)

*Primary Examiner* — Scott Long
(74) *Attorney, Agent, or Firm* — Jackson Walker L.L.P.

(57) ABSTRACT

Methods are provided for the treatment of diseases and disorders using systematically-introduced nanoparticles to create a focused localized hyperthermia in a target area to enhance the effect of additional treatment therapies such as ionizing radiation. Advantages include an enhancement of the therapeutic effect of other therapies by increasing perfusion or reducing hypoxia in the treatment area, further, the methods herein may also result in the disruption of the vasculature, which provide further impetus for such treatments, singly and in combination with conventional therapies such as chemotherapy and radiation therapy. Methods for treating a target area may comprise systemically introducing nanoparticles into an organism; allowing the nanoparticles to preferentially accumulate in the target area, applying an external energy where the nanoparticles are adapted to transduce at least a portion of the external energy into a heat energy so as to create a focused localized hyperthermia; and applying a subsequent additional therapy.

22 Claims, 8 Drawing Sheets

(56) References Cited

OTHER PUBLICATIONS

Ji, X., et al; Bifunctional Gold Nanoshells With a Superparamagnetic Iron Oxide-Silica Core Suitable for Both MR Imaging and Photothermal Therapy; J. Phys. Chem. C 2007, 111, pp. 6245-6251, Jan. 10, 2007.
Pawelek, J.M., et al; Bacteria As Tumour-Targeting Vectors; The Lancet Oncology, vol. 4, pp. 438-556, Sep. 4, 2003.
European Patent Office; Extended European Search Report; European Application No. 09702553.0; Aug. 3, 2011.
European Patent Office; Invitation Pursuant to Rule 63(1) EPC; Application No. 09 702 553.0; Mar. 23, 2011.
U.S. Appl. No. 61/011,266; "The Treatment of Disease or Disorders Using Energy-Absorbing Particles for Focused Hyperthermia to Increase the Efficacy of Other Therapies."
Moeller, B.J.; Richardson, R.A.; Dewhirst, M., W. Cancer Metastasis Rev. 2007, 26, (2), 241-48.
McDonald, D.M.; Choyke, PL., Nat Med 2003, 9, (6), 713-25.
Baluk, P.; Morikawa, S.; Haskell, A.; Mancuso, M.; McDonald, D.M., Am J Pathol 2003, 163, (5), 1801-15.
Harris, A.L., Nat Rev Cancer 2002, 2, (1), 38-47.
Hockel, M.; Vaupel, P., J Natl Cancer Inst 2001, 93, (4), 266-76.
Zhang, Y.; Li, M.; Yao, Q.; Chen, C., Med Sci Monit 2007, 13, (10), RA175-80.
Roti Roti, J.L. Int J. Hyperthermia 2004, 20, (2), 109-14.
Kampinga H.H.; Dikomey, E., Int J Radiat Biol 2001, 77, (4), 399-408.
Moros, E.G.; Cony, P.M.; Orton, C.G., Med Phys 2007, 34, (1), 1-4.
Gannon CJ, Patra CR, Bhattacharya R, Mukherjee P, Curley SA. "Intracellular gold nanoparticles enhance non-invasive radiofrequency thermal destruction of human gastrointestinal cancer cells." J Nanobiotechnology, Jan. 30, 2008;6:2.
Duff, D.G.; Baiker, A.; Edwards, P.P., Langumir 1993, 9, (9), 2301-2309).
Ishihara, Y.; Calderon, A.; Watanabe, H.; Okamoto, K.; Suzuki, Y.; Kuroda, K.; Suzuki, Y., Magn Reson Med 1995, 34, (6), 814-23.
Jain, P.K.; Lee, K.S.; El-Sayed, I.H.; El-Sayed, M.A., J Phys Chem B 2006, 110, (14), 7238-48.
Jain, R.K., Cancer Res 1988, 48, (10), 2641-58.
Brown, J.M., Methods Enzyrnol 2007, 435, 295-321.
Patterson, D.M.; Rustin, G., J. Clin Oncol (R Coll Radiol) 2007, 19, (6), 443-56.
Hinnen, P.; Eskens, F.A,, Br J Cancer 2007, 96, (8), 1159-65.
Jameson, M.B.; Baguley, B.C.; Kestell, P.; Zhao, L.; Paxton, J.W.; Thompson, P.I.; Waller, S., Cancer Chemother Pharmacol 2007, 59, (5), 681-7.
O'Hanlon, L.H., J. Nat'l Cancer Inst. 2005, 97, (17), 1244-5.
Lowery AR, Gobin AM, Day ES, Halas NJ, West JL., "Immunonanoshells for targeted photothermal ablation of tumor cells," Int J Nanomedicine, 2006, 1(2), 149-54.
Tozer, G.M.; Kanthou, C.; Baguley, B.C., Nat Rev Cancer 2005, 5, (6), 423-35.
Siemann, D.W.; Rajiani, A.M., Int J Radiat Oncol Biol Phys 2005, 62, (3), 846-53.
Siemann, D.W.; Horsman, M.R., Expert Rev Anticancer Ther 2004, (4), (2), 321-7.
Van Heeckeren, W.J.; Bhakta, S.; Ortiz, J.; Duerk, J.; Cooney, M.M.; Dowlati, A.; McCrae, K.; Remick, S.C., J Clin Oncol 2006, 24, (10), 1485-8.
Van Heeckeren, W.J.; Sanborn, S.L.; Narayan, A.; Cooney, M.M.; McCrae, K.R.; Schmaier, A.H.; Remick, S.C., Curr Opin Hematol 2007, 14, (5), 468-80.
Dings, R.P.; Loren, M.; Heun, H.; McNiel, E.; Griffioen, A.W.; Mayo, K.H.; Griffin, R., J Clin Cancer Res 2007, 13, (11), 3395-402.
Winkler, F.; Kozin, S.V.; Tong, R.T.; Chae, S.S.; Booth, M.F.; Garkavtsev, I.; Xu, L.; Hicklin, D.J.; Fukumura, D.; di Tomaso, E.; Munn, L.L.; Jain, R.K., Cancer Cell 2004, 6, (6), 553-63.
Hainfeld, J.F.; Slatkin, D.N.; Smilowitz, H.M., Phys Med Biol 2004, 49, (18), N309-15.
Liu Z, Cal W, He L, Nakayama N, Chen K, Sun X, Chen X, Dai H "In vivo biodistribution and highly efficient tumour targeting of carbon nanotubes in mice," Nat Nanotechnol. Jan. 2, 2007(1):47-52.
European Patent Office; Response to Office Action; European Application No. 09 702 553.0; Jul. 12, 2013, 7 pages.

* cited by examiner

TREATMENTS OF DISEASE OR DISORDERS USING NANOPARTICLES FOR FOCUSED HYPERTHERMIA TO INCREASE THERAPY EFFICACY

CROSS-REFERENCE TO RELATED APPLICATION

The patent application claims priority to and the benefit of U.S. Provisional Patent Application Ser. No. 61/011,266, titled, "The Treatment of Disease or Disorders Using Energy-Absorbing Particles for Focused Hyperthermia to Increase the Efficacy of Other Therapies," the entire specification of which is hereby incorporated by reference.

BACKGROUND

The present invention generally relates to methods for the treatment of a variety of diseases and disorders utilizing systemically-introduced nanoparticles to create focused hyperthermia of a target area so as to enhance the efficacy of additional therapies.

Radiation therapy is often a component of the multidisciplinary approach to the treatment of many tumors. However, as a single modality, radiation therapy is unable to eradicate all locoregional recurrences and/or cure localized cancers. This ineffectiveness is largely related to the intrinsic resistance of some cancer cells to ionizing radiation. Moeller, B. J.; Richardson, R. A.; Dewhirst, M., *W. Cancer Metastasis Rev.* 2007, 26, (2), 241-48.

Intratumoral hypoxia is believed to be a key mediator of this resistance to radiation therapy and is exacerbated by inadequate oxygenation via mutated, chaotic and incomplete blood vessels in tumors. McDonald, D. M.; Choyke, P. L. *Nat Med* 2003, 9, (6), 713-25; Baluk, P.; Morikawa, S.; Haskell, A.; Mancuso, M.; McDonald, D. M., *Am J Pathol* 2003, 163, (5), 1801-15. Hypoxia is known to induce the expression of a spectrum of genes involved in metabolism, proliferation, apoptosis, and angiogenesis. Harris, A. L., *Nat Rev Cancer* 2002, 2, (I), 38-47; Hockel, M.; Vaupel, P., *J Natl Cancer Inst* 2001, 93, (4), 266-76; These hypoxia-induced tumor cellular and microenvironmental changes contribute to tumor aggressiveness and resistance to radiation therapy. Zhang, Y.; Li, M.; Yao, Q.; Chen, C. *Med Sci Monit* 2007, 13, (10), RA 175-80. Consequently, any therapeutic strategy that alleviates tissue hypoxia could potentially overcome a major mechanism of radioresistance and enhance the effects of radiation therapy.

One such highly effective therapeutic adjunct to radiation therapy is mild temperature hyperthermia, which has direct anti-tumor effects and tumor microenvironment effects mediated, in part, through mitigation of hypoxia that contribute to the observed radio-insensitization. Roti Roti, J. L. *Int J Hyperthermia* 2004, 20, (2), 109-14; Kampinga, H. H.; Dikomey, E. *Int J Radial Biol* 2001, 77, (4), 399-408; Moros, E. G.; Corry, P. M.; Orton, C. G. *Med Phys* 2007, 34, (1), 1-4. Mild temperature hyperthermia mediates its anti-tumor effects via subtle influences on the tumor microenvironment, activation of immunological processes, induction of gene expression and induction of protein synthesis. While these effects do not independently cause tumor cell cytotoxicity, they lead to greater effectiveness of other conventional treatment modalities such as radiation therapy, chemotherapy and immunotherapy. In particular, in its role as an adjunct to radiation therapy, hyperthermia serves as a dose-modifying agent that increases the therapeutic ratio of radiation therapy, i.e. enhanced effectiveness without additional toxicity.

Various methods have been used to combine hyperthermia and radiotherapy. One example included applying interstitial radiation with interstitial hyperthermia in brain tumors. Another example used magnetic particles directly injected into a tumor and external beam radiation. Recently, iron oxide particles have been directly injected into a tumor and an alternating magnetic field applied for hyperthermia followed by ionizing radiation.

As another example, in U.S. Pat. No. 5,620,479, Diederich describes a method and apparatus for thermal therapy of tumors using piezoceramic tubular transducers for the delivery of interstitial thermal therapy in conjunction with simultaneous brachytherapy or radiotherapy from within the applicator. In yet another example, in U.S. Pat. No. 6,957,108, Turner et al. describe a microwave hyperthermia apparatus that can be inserted into the body that includes a hollow central tube for the insertion of radioactive therapy sources for hyperthermia and brachytherapy.

Several randomized trials have demonstrated improved response rates and survival when patients with locally advanced malignancies are treated with locoregional hyperthermia and radiotherapy compared to radiotherapy alone. Despite convincing evidence for hyperthermic radiosensitization, it is underutilized in routine clinical practice for the following reasons: (a) the invasive means of achieving and maintaining hyperthermia, (b) the time commitment involved in a treatment, which can often last about an hour, (c) the lack of good thermal dosimetry and (d) the inability to achieve localized hyperthermic temperatures. Thus, conventional methods for utilizing hyperthermia to enhance other treatment therapies suffer from a variety of disadvantages.

A localized dose enhancement of ionizing radiation can also result from the presence of certain elements in the tumor. For example, in U.S. Pat. No. 7,367,934. Hainfeld et al. describe the use of heavy metal particles delivered to a tissue or cells to achieve a concentration within the tissue of at least 0.1% metal by weight, applying ionizing radiation of specified energy and achieving a localized radiation dose enhancement. The radiation enhancement achieved from the interaction of the metal and the radiation, requiring a minimum metal content for efficacy.

As an alternative approach to cancer therapy, vascular disruptive agents ("VIDA") are being developed in an attempt to treat cancer through the elimination or disruption of the blood supply. These agents may also be used in conjunction with ionizing radiation. Vascular disruption of a single established blood vessel, be it via subtle structural changes of dysmorphic endothelial cells or induction of intravascular coagulation, could potentially eliminate hundreds or thousands of tumor cells downstream. Vascular disrupting agents in preclinical and early clinical development include combretastatin A4 phosphate (CA4P), ZD6126, TZT-1027, AVE8062, ABT-751, and MN-029, which target the tubulin cytoskeletal network of endothelial cells; 5,6-dimethylxanthenone-4-acetic acid (DMXAA), which targets autocrine endothelial regulatory cascades; and exherin (AFH-1), which targets cell adhesion. While these agents have shown promise in early trials, there is concern that more than just tumor vessels may be targeted by systemic exposure to these agents. In particular, damage to vascular compartments outside the tumor may contribute to acute coronary syndromes and thromboembolic events. Consequently, conventional treatment methods lack the ability to focus such treatments on specific target areas.

While a principal use of ionizing radiation is in the treatment of cancer, other diseases and disorders may benefit from radiotherapy if the ionizing effects could be confined to the target area or, alternatively, if the target area could be sensitized to the effects of ionizing radiation by a non-invasive method. For example, there are other medical conditions in which disruption of the vasculature is desired, such as arteriovenous malformations (AVMs), which can result in hemorrhage or other deleterious effects depending on their location (in case of brain AVMs, seizures and aberrant vascular perfusion of adjacent normal brain).

Accordingly, improved treatment methods are needed to address one or more of the disadvantages of the prior art.

SUMMARY

The present invention generally relates to methods for the treatment of a variety of diseases and disorders utilizing systemically-introduced nanoparticles to create focused hyperthermia of a target area so as to enhance the efficacy of additional therapies.

An example of a method for the treatment of a tumor residing in a target area of an organism comprises the steps of: systemically introducing a plurality of nanoparticles into a circulating blood of an organism; allowing the nanoparticles to preferentially accumulate in the target area; allowing application of an external energy to the target area wherein the nanoparticles are adapted to transduce at least a portion of the external energy into heat energy wherein the external energy is an electromagnetic or a mechanical energy; allowing the temperature of the area of accumulation of the nanoparticles to elevate to a localized elevated temperature by way of a transduction of the external energy into heat energy by the nanoparticles; and applying ionizing radiation to the target area.

An example of a method for the disruption of a vasculature of a target area comprises the steps of: systemically introducing a plurality of nanoparticles into a circulating blood of an organism; allowing the nanoparticles to preferentially accumulate in the target area; allowing application of an external energy to the target area wherein the nanoparticles are adapted to transduce at least a portion of the external energy into heat energy wherein the external energy is an electromagnetic or a mechanical energy; allowing a temperature of the target area to elevate to a localized elevated temperature by way of a transduction of the external energy into heat energy by the nanoparticles; and applying ionizing radiation to the target area so as to disrupt the vasculature of the target area.

An example of a method for the disruption of a vasculature of a target area comprises the steps of: allowing application of an external energy to the target area wherein the target area transduces at least a portion of the external energy into heat energy wherein the external energy is an electromagnetic or a mechanical energy; allowing a temperature of the target area to elevate to a localized elevated temperature by way of a transduction of the external energy into heat energy; and applying ionizing radiation to the target area so as to disrupt the vasculature of the target area.

An example of a method for the disruption of a vasculature of a target area comprises the steps of: applying electromagnetic energy to the target area wherein the electromagnetic energy is in a wavelength absorbed by a blood component of the target area; allowing the applied electromagnetic energy to result in an elevated temperature of the vasculature of the target area; and applying ionizing radiation to the target area so as to disrupt the vasculature of the target area.

The features and advantages of the present invention will be apparent to those skilled in the art. While numerous changes may be made by those skilled in the art, such changes are within the spirit of the invention.

BRIEF DESCRIPTION OF THE DRAWINGS

A more complete understanding of the present disclosure and advantages thereof may be acquired by referring to the following description taken in conjunction with the accompanying figures, wherein:

FIG. 1$b$ illustrates a temperature profile of tumor tissue measured by thermocouples.

FIG. 1$c$ illustrates MRTI images of tumor tissues at various time periods.

FIG. 1$d$ illustrates temperature profile in tumor tissue estimated from the MRTI at various time points during laser illumination at 024 h after gold nanoshell injection.

FIG. 2$b$ illustrates the corresponding tumor doubling time after each treatment.

Figures 1A, 1B:
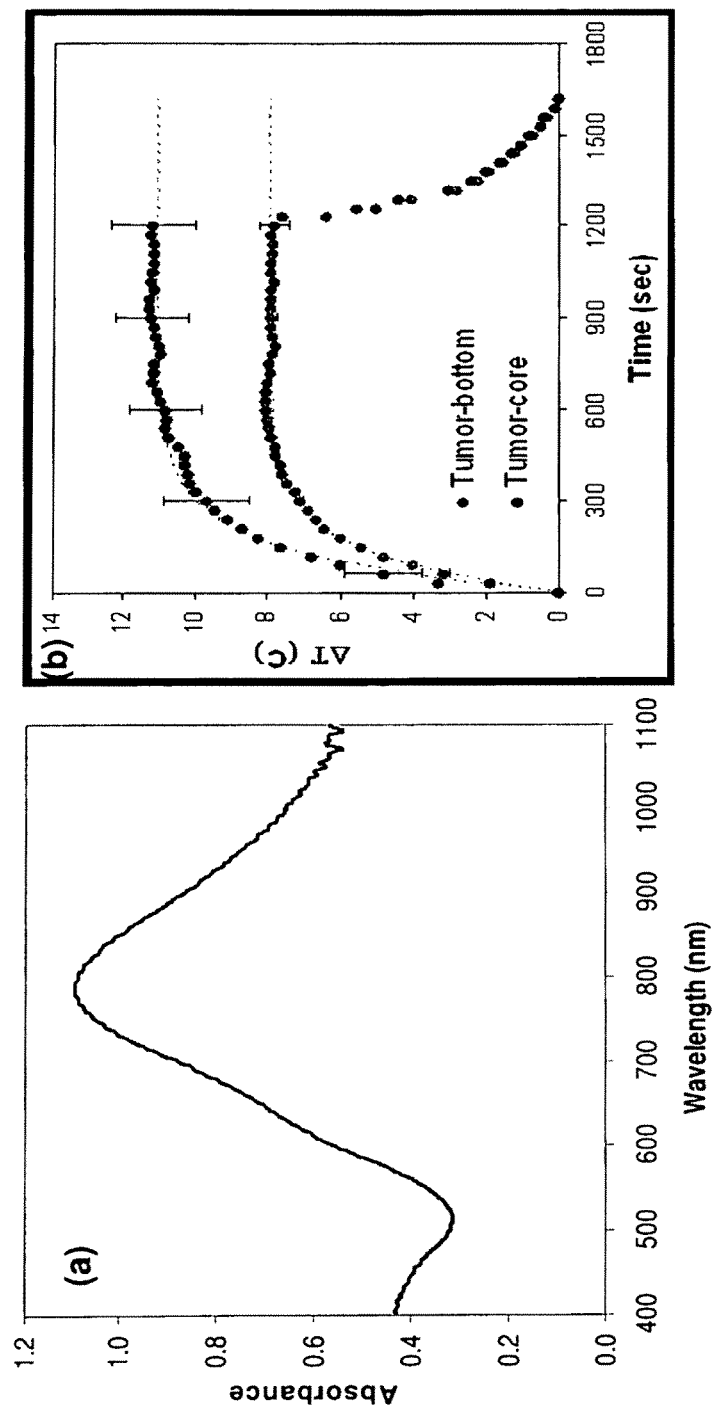
FIG. 1$a$ illustrates absorption spectra of gold nanoshells (silica core diam: 120±12 nm; gold shell diam: 12±3 nm).

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF PREFERRED EMBODIMENTS

The present invention generally relates to methods for the treatment of a variety of diseases and disorders utilizing systemically-introduced nanoparticles to create focused hyperthermia of a target area so as to enhance the efficacy of additional therapies.

Generally, the present invention describes a method for treating tumors or target tissues using localized hyperthermia to enhance the effect of other therapies such as drug treatments and radiation treatments.

In certain embodiments, methods are provided for the treatment of diseases and disorders using systemically-introduced nanoparticles to create a focused localized hyperthermia in a target area so as to enhance the effect of an additional treatment therapy such as ionizing radiation. Advantages of the methods herein include an increase of the therapeutic effect of other therapies by increasing perfusion or reducing hypoxia in the treatment area. Further, in certain embodiments, the methods herein may also result in the disruption of the vasculature, which provide further impetus for such treatments, singly and in combination with conventional therapies such as anti-hypoxic agents. Although the examples provided herein relate in large part to the treatment of tumors, it is explicitly recognized that the methods herein may be used to treat any disease or disorder that would be enhanced by the creation of a localized hyperthermia, such as, for example, vascular conditions.

To facilitate a better understanding of the present invention, the following examples of certain embodiments are given. In no way should the following examples be read to limit, or define, the scope of the invention.

In certain embodiments, methods for treating a tumor residing in a target area of an organism comprise in part:

(a) systemically introducing a plurality of nanoparticles into a circulating blood of the organism;

(b) allowing the nanoparticles to preferentially accumulate in the target area of the organism;

(c) applying an external energy to the target area wherein the nanoparticles are adapted to transduce at least a portion of the external energy into a heat energy;

(d) allowing the heat energy to elevate the temperature of the target area so as to create a focused localized hyperthermia; and (e) applying a subsequent additional therapy.

Each of these steps will now be discussed. An organism has a disease or disorder, such as a tumor, residing, at least partially, in a target area. In step (a), a plurality of nanoparticles is systemically introduced into the circulating blood of the organism via injection. In step (b), the nanoparticles are allowed to preferentially accumulate in a target area of the organism. This accumulation of nanoparticles in the target area may occur passively through the enhanced permeability and retention ("EPR") effect or through active targeting mechanisms, both of which are described below in more detail.

In step (c), an external energy is applied to the target area via an external energy source. The external energy may be any electromagnetic energy or a mechanical energy. Suitable forms of electromagnetic energy include, but are not limited to, ultraviolet radiation, visible light, infrared light, microwave radiation, radiowaves, alternating magnetic fields, or any combination thereof. Suitable forms of mechanical energy include, but are not limited to, acoustic energy such as ultrasonic waves.

External energy is then transduced to heat at least partially by the nanoparticles that have accumulated in the target area. In this way, the transduction of energy by the nanoparticles induces a localized temperature elevation or hyperthermia confined to the target area and the region immediately adjacent thereto. Accordingly, the target area is sensitized to subsequent therapies, and effects on surrounding healthy tissue are minimized.

Upon achieving a localized focused hyperthermia in the target area, a subsequent additional therapy may be applied to the target area. As described in more detail below, suitable additional therapies include, but are not limited to, ionizing radiation, a hypoxia-targeted therapy, a therapeutic agent, or any combination thereof. In certain embodiments, ionizing radiation may optionally be applied via an external energy source. In certain embodiments, the additional therapy may be a hypoxia-targeted therapy or a therapeutic agent delivered via systemic introduction or direct injection to the target area 120.

Suitable Nanoparticles

Nanoparticles suitable for use in conjunction with the present invention include any nanoparticle that is adapted to at least partially transduce an external energy into heat energy for elevating the temperature of a target area. Suitable examples of such materials and their methods of production and functionalization are known in the art. See e.g., U.S. Pat. Nos. 6,344,272 and 6,685,986. These transducing nanoparticles include, among others: nanoshells (including gold-shell silica core nanoshells, gold-gold sulfide nanoshells and other variants), metal nanorods, nanostars, hollow nanoparticles, nanocages, elliptical "nanorice," carbon particles, fullerenes, carbon fullerenes, metallic nanoparticles, metal colloids, carbon particles, carbon nanotubes, buckyballs, and any combination thereof.

In certain embodiments, the nanoparticles may be a magnetic or paramagnetic (e.g., iron oxide particles) particularly when the energy source is an alternating magnetic field. In another embodiment, the nanoparticles may be a conducting material (e.g., gold or other metal colloids, nanoshells, nanorods, buckeyballs and carbon nanotubes), particularly when the energy source is radiowaves. Carbon fullerenes, nanocubes, nanostars, and indocyanine green encapsulated in nanoparticles may also be used as suitable nanoparticles.

In certain embodiments, the nanoparticles may be designed or selected to absorb near-infrared energy, light in the visible spectra, radiowaves, microwaves, magnetic energy, other forms of electromagnetic radiation, or any combination thereof. Alternatively, these particles can be designed to absorb mechanical energy such as acoustic waves, for example, ultrasound waves.

In certain embodiments, more than one type of nanoparticle may be simultaneously used. Each type of nanoparticle may be designed or tuned to preferentially transduce a different type of external energy.

In more particular embodiments, nanoparticles may be designed to absorb electromagnetic radiation in the near-infrared region (e.g. between 670 nm and 1200 nm), wavelengths that allow the maximum penetration of this energy through normal tissue. Upon the application of a laser emitting within these wavelengths, the nanoparticles absorb and convert this energy into heat to elevate the temperature of the tumor to a non-ablative level, increasing the sensitivity of the tumor to a subsequent therapy, such as ionizing radiation. The effect of the nanoshell-induced hyperthermia is to create a temperature elevation confined to the tumor and the region immediately adjacent thereto, localizing the area of increased sensitivity to ionizing radiation to minimize the effect on surrounding healthy tissue.

These particles can be delivered to the tumor by injection or by systemic delivery, with or without targeting mechanisms. As described further below, these particles may optionally be targeted to the vasculature associated with the tumor. As used herein, the term "nanoparticle" also includes particles of a size that may be systemically be delivered to the target area through the blood stream or lymphatic channels. In certain embodiments, a nanoparticle will have a largest dimension of less than 1 micron, and in other embodiments, preferably less than 200 nanometers.

Systemic Introduction and Accumulation of Nanoparticles in the Target Area

The nanoparticles may be systemically introduced into the organism to be treated. As used herein, the term "systemic introduction" refers to any introduction of nanoparticles that pertains to or affects the organism as a whole such as an introduction of nanoparticles into the circulating blood of an organism. As previously described, the mechanism by which the nanoparticles accumulate in the target area may be by a passive mechanism, an active mechanism, or a combination thereof.

In the passive mechanism, nanoparticles may be injected or infused into the blood stream and accumulate at the target area or tumor site through the enhanced permeability and retention ("EPR") effect. Through this mechanism, passively targeted particles accumulate in the tumor in a region near the disrupted blood vessels. In certain embodiments, gold nanoshells measuring about 150-160 nm, when injected intravenously, accumulate preferentially in tumors by the enhanced permeability and retention (EPR) effect, where the leaky tumor vasculature containing wide interendothelial junctions, abundant transendothelial channels, incomplete or absent basement membranes, and dysfunctional lymphatics contribute to passive extravasation of systemically injected macromolecules and nanoparticles into tumors.

Active mechanisms for targeting the tumor site include conjugating nanoparticles with an antibody to a cell surface molecule, such as an anti-EGFr antibody, preferentially expressed by a target cell. These particles may be inserted into the blood, allowed to selectively accumulate in the target area, and selectively bind to cells in the target area which have such molecules present on their cell surface. Additionally, vascular targeting agents (e.g., ligands for the integrin alpha.v beta.3, VEGFr or phosphatidylserine) may be used to actively target the target site. Similarly, particles actively targeted to the tumor endothelial cells will accumulate at an endothelial surface.

A variety of ligands may be selected for use to preferentially associate the exogenous material with the target cells. The attachment of these ligands to exogenous materials has been extensively described in the scientific literature. The choice of ligand is dependent on the target cells. For example, if the target is a tumor cell that expresses the HER2 receptor, molecules that selectively bind to the HER2 receptor may be used. Alternatively, the ligand may be selected for affinity to the, the EGF receptor, an integrin, a hormonal receptor, or a variety of other surface molecules. One of ordinary skill in the art, with the benefit of this disclosure, will appreciate, that the ligand may be selected from a variety of proteins, peptides, antibodies, antibody fragments, aptamers or other compounds that has a preferential affinity for the target over other circulating blood components. The ligand(s) selected need not be specific for only the target.

Application of External Energy to the Target Area

The external energy may be applied from a position external to the body or from an applicator placed within or near the target area. The external energy may comprise electromagnetic radiation, mechanical energy, or any combination thereof. Suitable forms of electromagnetic energy include, but are not limited to, ultraviolet radiation, visible light, infrared light, microwave radiation, radiowaves, alternating magnetic fields, or any combination thereof. Suitable forms of mechanical energy include, but are not limited to, acoustic energy such as ultrasonic waves.

Typically, the external energy will be selected to correspond to the type of energy to which the nanoparticles preferentially transduce. In certain embodiments, more than one type of external energy may be used simultaneously or in sequence, particularly where more than one type of nanoparticle is present in the target area.

Generally, the external energy will be limited to a non-ablative level that generates a focused localized hyperthermia. Nevertheless, in certain embodiments, the external energy is applied in a manner which both generates a focused localized hyperthermia and, causes the nanoparticles to ablate adjacent or targeted cells.

Focused Localized Hyperthermia

The application of energy to these passively or actively targeted nanoparticles will result in hyperthermia localized within the target area, but more specifically in the area proximate to the nanoparticle accumulations in the target area. These accumulations may occur near the related vasculature or at the surface f target cells. This non-invasive method of producing a focused localized hyperthermia overcomes a number of the disadvantages previously noted in the prior art.

Indeed, this type of non-invasive method to generate focused localized hyperthermia in a target area is especially beneficial for such treatments as hyperthermic sensitization of tumors to chemotherapy (via increased vascular perfusion of areas of the tumor that are otherwise shielded from exposure to chemotherapy drugs due to inadequate blood supply) and hyperthermia-mediated delivery of chemotherapy drug encapsulated in a temperature-sensitive liposome.

Thus, by increasing perfusion or reducing hypoxia in the treatment or target area, the efficacies of subsequent therapies may be enhanced. Because of this enhanced efficacy of the subsequent therapies, dose reductions of the subsequent therapies may be realized. These dose reductions may especially beneficial in subsequent therapies such as ionizing radiation where the ionizing radiation poses increased independent risks of adverse effects. Thus, by minimizing the effective dose of a subsequent therapy, any adverse effects of a subsequent therapy can be minimized.

Applying a Subsequent Therapy

Upon generating focused localized hyperthermia in the target area, a subsequent therapy may be applied to the target area. Suitable additional therapies include, but are not limited to, ionizing radiation, a hypoxia-targeted therapy, a therapeutic agent, or any combination thereof. Where the additional therapy is a hypoxia-targeted therapy or a therapeutic agent, it may be delivered via systemic introduction into the circulating blood of the organism or by direct injection to target area to be treated.

Where ionizing radiation is the additional therapy applied, it may be applied from an external source, an internal source (as in Systemic Targeted Radionuclide Therapy), or alternatively from a localized source such as brachytherapy seeds. The ionizing radiation may be applied in a single dose or in multiple doses over time. This technique of using ionizing radiation following a focused localized hyperthermia is referred to herein as thermoradiotherapy.

The subsequent application of ionizing radiation may have a pronounced effect resulting in the disruption of the cells situated in the area of preferential nanoparticle accumulation. Where such nanoparticle accumulation is concentrated near the tumor vasculature The subsequent application of ionizing radiation may have a pronounced effect resulting in the disruption of the tumor vasculature. This effect, although in some cases similar to that achieved by vascular disrupting agents currently being investigated, is localized to the tumor that is preferentially exposed to hyperthermia and radiation so as to eliminate the side effects normally associated with conventional systemically active VDAs.

Alternatively, the use of particle-based localized hyperthermia and ionizing radiation may be used to treat other diseases and disorders, including vascular disorders, such as arteriovenous malformations.

Alternatively, the energy-absorbing properties of the target area may be used to deliver a localized hyperthermia to the vasculature. In such an embodiment, the absorption properties of the target, such as a high level of hemoglobin related to the higher blood content of the target, may be used in conjunction with a localized near-infrared laser to deliver a localized hyperthermia to the vasculature of a target area in conjunction with ionizing radiation to create a disruption of the vasculature of the area.

The localized hyperthermia may be used to initially reduce the hypoxia or increase the perfusion of the target area. This increased perfusion may enhance the effect of other therapeutic agents. When applied in conjunction with ionizing radiation, the subsequent vascular disruption can result in a level of necrosis through reduction of vessel density. Accordingly, this method of localized hyperthermia and related vasculature disruption or necrosis may result in increased hypoxia/anoxia in the target area subsequent to this initial therapy, which may also be used with agents or methods that use or require hypoxia for therapy.

It is explicitly recognized that any of the elements and features of each of the devices described herein are capable of use with any of the other devices described herein with no limitation. Furthermore, it is explicitly recognized that the steps of the methods herein may be performed in any order except unless explicitly stated otherwise or inherently required otherwise by the particular method.

EXAMPLES

To facilitate a better understanding of the present invention, the following examples of certain aspects of some embodiments are given. In no way should the following examples be read to limit, or define, the scope of the invention.

The following examples demonstrate modulation of in vivo tumor radiation response using gold nanoshell-mediated hyperthermia via a dual vascular-focused mechanism: (a) an early increase in perfusion that reduces the radioresistant hypoxic fraction of tumors and (b) a subsequent induction of vascular disruption/collapse and extensive necrosis that complements radiation-induced cell death. These tumor vasculature focused effects characterize a novel agent/device (gold nanoshells) that serves as an integrated anti-hypoxic and localized vascular disrupting agent.

Production of Nanoparticles.

Gold nanoshells were fabricated as follows. Colloidal silica (120 nm±12 nm diameter) was used as the core material (Precision Colloids, LLC). Gold colloids of ~1-3 nm in diameter were grown by using the method of Duff (Duff, D. G.; Baiker, A.; Edwards, P. P. *Langumir* 1993, 9, (9), 2301-2309) and aged for 2 weeks at 4° C. and the aged gold colloid suspension was mixed with aminated silica particles. Gold colloid adsorbs to the amine groups on the surface of the silica core to form nucleating sites, which were further reacted with $HAuCl_4$ in the presence of formaldehyde. This process reduces additional gold onto the adsorbed colloid, which acts as a nucleation site, causing the surface colloid to grow and coalesce with neighboring gold colloid, forming a complete metal shell. Particles were designed to have a 120 nm core diameter and a 12-15 nm-thick shell resulting in an absorption peak between 780 and 800 nm (FIG. 1-*a*), assessed by a UV-VIS spectrophotometer. For passive targeting, a thiolated polyethylene glycol SH-PEG (Laysan Bio, Huntsville, Ala.) was assembled onto nanoshell surfaces by combining 5 μM SH-PEG and nanoshells in DI $H_2O$ (~3.2×10$^5$ SH-PEG molecules/particle) for 12 hrs, followed by diafiltration to remove the excess SH-PEG. Resulting particles were coated with an average of 3.2×10$^5$ SH-PEG molecules and suspended in 10% trehalose solution to create an iso-osmotic solution for injection.

Localized Mild-Temperature Hyperthermia can be Induced Non-Invasively by Optically Activated Gold Nanoshells and Measured Non-Invasively by Magnetic Resonance Thermal Imaging (MRTI).

Figures 1C, 1D:
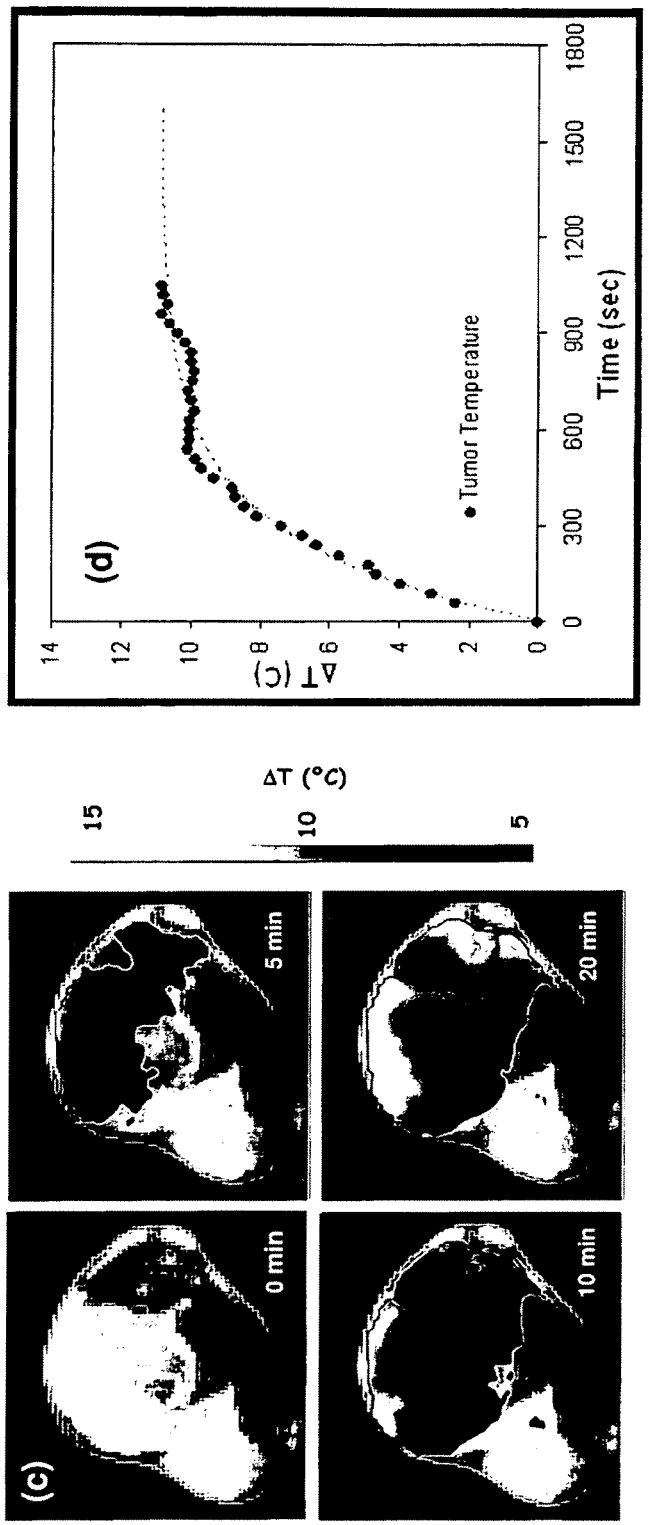

To optimize the laser settings for generation of mild-temperature hyperthermia over a short period of time without significant over-heating of both tumor and/or surrounding normal tissues, temperature increases were initially recorded under different laser illumination conditions in an in vivo tumor model using tumor-implanted thermocouples. Six to eight-week-old immunocompromised male nude (Swiss nu/nu) mice weighing 20-25 g each were subcutaneously inoculated with human colorectal cancer cells (HCT 116; ~2×10$^6$ cells per 50 μl of sterile phosphate buffered saline) in the right thigh. When the tumors attained a size of ~7-8 mm in diameter, ~8×10$^8$ nanoshells/g body weight (or ~14 μg/g body weight) were injected intravenously via the tail vein. Localized hyperthermia was carried out at 20-24 hrs post-injection, needle thermocouples (model HYP1-30-1/2-T-G-60-SMP-M, Omega Engineering) were positioned in the tumor core and tumor base (adjacent to muscular fascia), and core body temperature was measured using a rectal probe (model RET-3, Braintree Scientific, Inc.). The three different laser settings evaluated were 0.8, 0.6 and 0.4 W/cm$^2$ in cohorts of 2-3 mice each. Prior to laser illumination PEG diacrylate (M, 600, Sartomer, West Chester, Pa.) was applied over the surface of the tumor as an index-matching agent. An 808 nm NIR diode laser (Diomed-plus 15, Diomed corp, UK) was used to illuminate the tumor surface (10 mm diameter spot size) via a fiber optic cable with a collimating lens. Average baseline tumor temperature was ~30±1° C. Upon illumination with a laser power of 0.8 W/cm$^2$, a steep rise in tumor temperature was observed within the first 5 min, followed by a steady temperature plateau (ΔT of ~13-15° C.) for the remaining 15 min of laser illumination. While this was still below the typical hyperthermia temperature threshold (<45° C.), because the intent was to generate mild-temperature hyperthermia without inducing tissue damage by the hyperthermia itself, and a lower power setting was chosen. Illumination with a laser power of 0.4 W/cm$^2$ achieved a ΔT of ~4-5° C. in the tumor core. Using an intermediate laser power of 0.6 W/cm$^2$, yielded ΔTs of ~10±1.5° C. and ~8±0.5° C. in the tumor core and base, respectively (FIG. 1-$b$). These illumination parameters (808 nm NIR laser beam, power setting of 0.6 W/cm$^2$, 75% duty cycle, final optical power output of ~350 mW/cm$^2$ at a spot size of 10 mm) were verified for reproducibility in an additional cohort of mice and then chosen for all subsequent hyperthermia experiments. The observed differences in temperature between the tumor core and base were attributable to (a) the limitation in depth of penetration of the NIR laser beam within tumor tissues, (b) the absorption of NIR light by the gold nanoshells in the superficial layers of the tissues and (c) the preferential accumulation of and absorption of NIR light by gold nanoshells within the perivascular space of blood vessels lining the periphery of the tumor. To further confirm that the induced temperature rise was mediated by gold nanoshells, temperature measurements were undertaken using identical laser settings in a cohort of control animals without nanoshells. ΔTs of ~2.5-3.5° C. were observed in the tumor core, the base of the tumor and in irradiated muscle of the contralateral thigh.

The thermocouple measurements were subsequently validated by non-invasive in vivo MRTI in an additional cohort of mice (see supplementary information below for additional details). Upon laser illumination with a power of 0.6 W/cm$^2$, real-time MRTI measurements demonstrated a temperature difference (ΔT) of ~11.0° C. consistent with the thermocouple measurements. The T1-weighted images overlaid with the temperature distribution images at 0, 5, 10 and 20 minutes after laser illumination are illustrated in FIG. 1$c$. The ΔT of ~15.0° C. observed in the tumor periphery (MRTI) may be attributable to the high concentration of nanoshells within the highly vascularized tumor periphery. Regions of Interest (ROIs) encompassing the whole tumor, tumor periphery and tumor core were created and averaged to generate temperature plots at various time points. A similar ROI from the background region was selected to compensate for background temperature changes. The temperature rise calculated from the real-time MRTI measurements is illustrated in FIG. 1-$d$. Similar to the thermocouple measurements, an initial steep rise in temperature was followed by a relatively sustained plateau region for the remaining period of laser illumination. However, the slope of the initial temperature rise was different from that of the thermocouple measurements, possibly attributable to the averaging of temperature across a larger ROI in the MRTI measurements as opposed to point measurements using the thermocouple.

Gold Nanoshell-Mediated Hyperthermia Enhances the Efficacy of Radiation Therapy.

Figure 2:
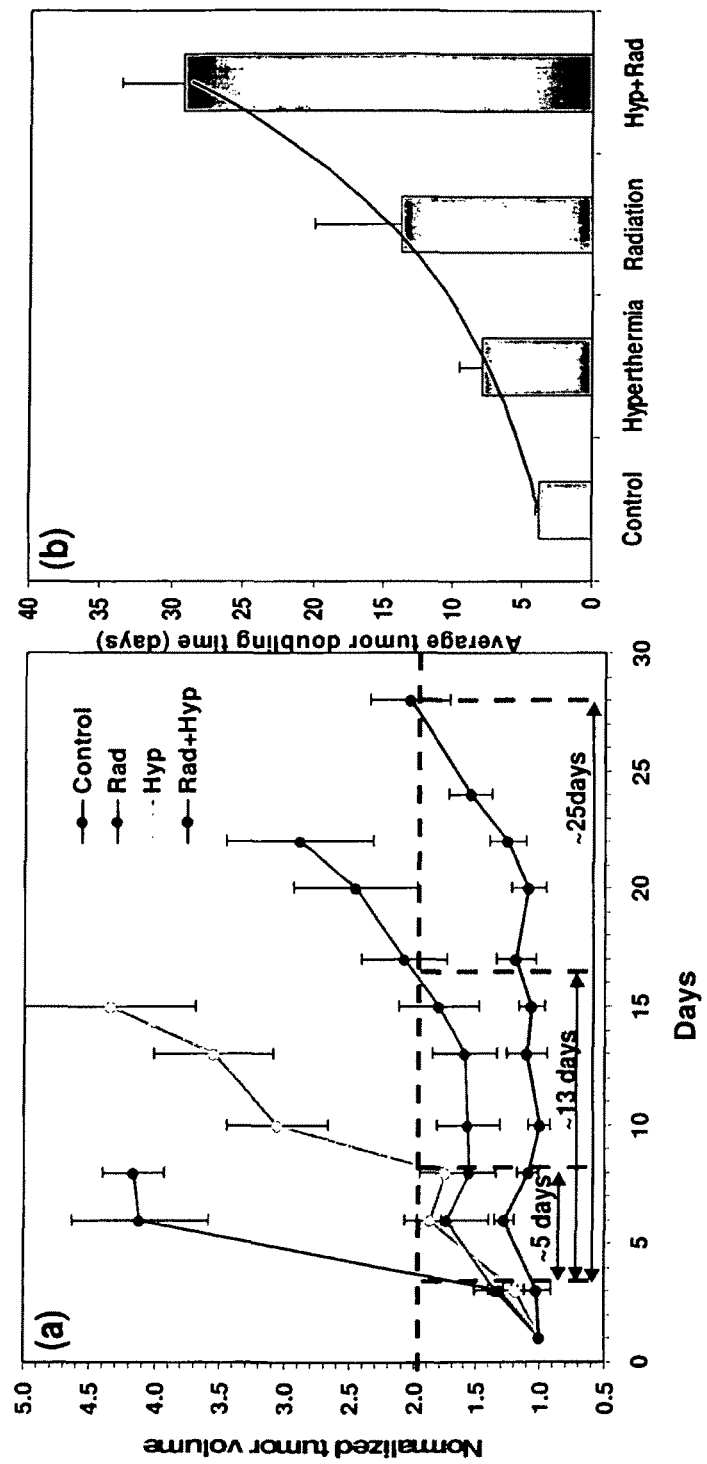
FIG. 2$a$ illustrates normalized tumor volume plot of control, hyperthermia, radiation, and thermoradiotherapy groups showing the mean±SE values at different time periods after the initiation of each treatment.

In a separate experiment employing the tumor re-growth delay assay, 36 mice bearing ~7-8 mm diameter tumors were evenly randomized to one of four treatment conditions: (a) control treatment with gold nanoshells alone without hyperthermia or radiation, (b) 20 min of laser illumination as specified above for generation of mild-temperature hyperthermia, (c) a single 10 Gy dose of radiation therapy using 125 kV X-rays (Phillips RT-250 orthovoltage X-ray unit operated at 20 mA and using a 2 mm Aluminum filter and a skin cone of 1 cm diameter to collimate the beam to the tumor surface with the target to surface distance of 22.4 cm; see supplementary information for experimental setup), and (d) hyperthermia followed by 10 Gy radiation therapy (thermoradiotherapy) ~3-5 min later. Tumor growth was followed by serially measuring tumor dimensions in two orthogonal directions (long axis: $a_1$; short axis: $a_2$) twice weekly. Tumor volume was calculated using the expression $(\pi/6).(a_1).(a_2)^2$ and plotted over time as represented in FIG. 2-$a$. The tumor volume of individual mice in each treatment group was normalized with respect to the initial tumor volume prior to treatment. Tumor re-growth delays, calculated as the time to doubling of tumor volume, were observed to be approximately 4, 9, 17, and 29 days for the control, hyperthermia, radiation and thermoradiotherapy groups, respectively. As illustrated in FIG. 2-$b$, there was a statistically significant ($p<0.005$) difference in tumor doubling time between the radiation and thermoradiotherapy groups.

Gold Nanoshell-Mediated Hyperthermia Enhances Perfusion.

Figures 3A, 3B, 3C, 3D, 3E, 3F:
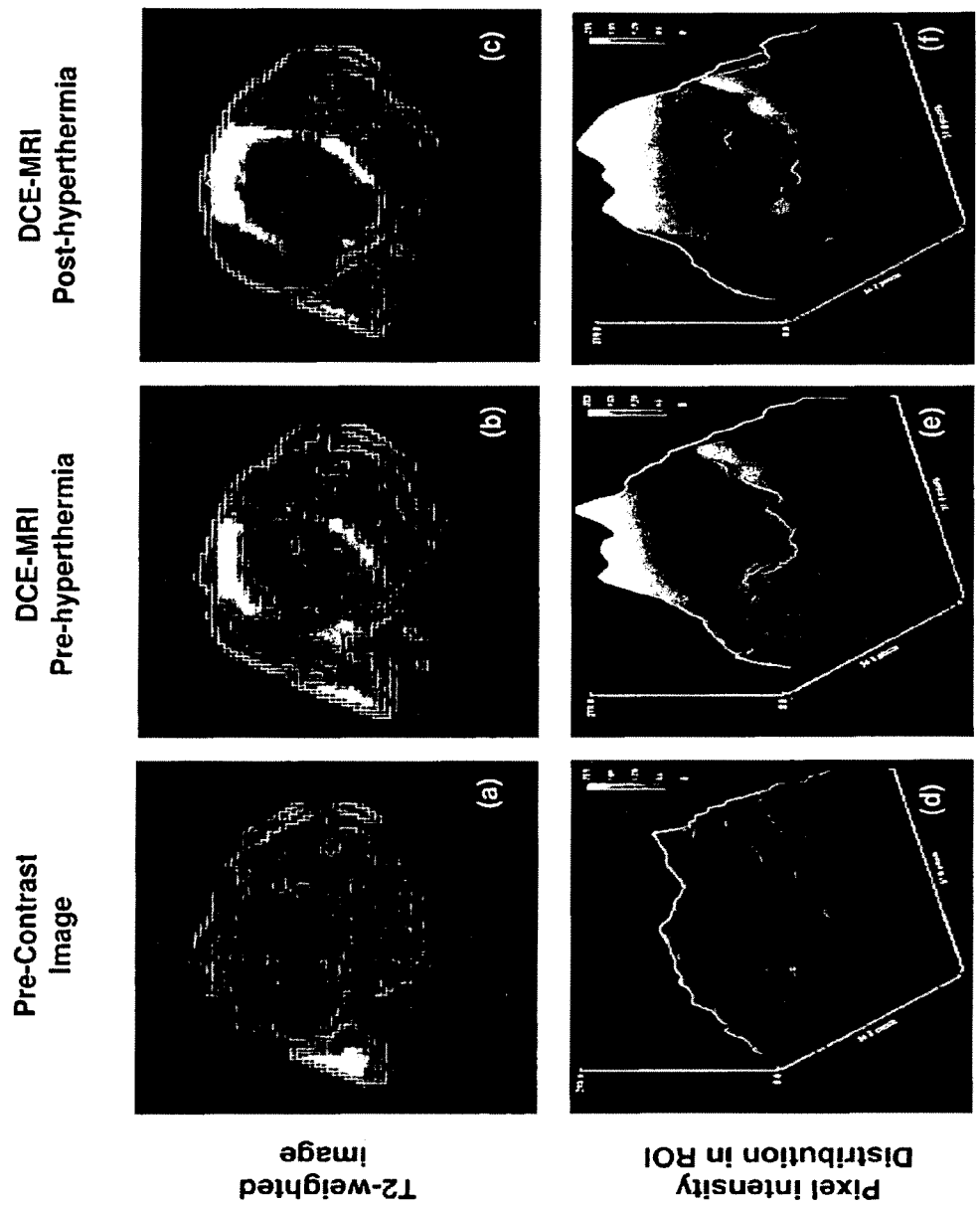
FIGS. 3$a$-$h$ illustrate T1-weighted (a) precontrast, (b) prehyperthermia DCE-MRI, (c) posthyperthermia DCE-MRI images of tumor, and (d-f) the corresponding 3D pixel intensity distribution profile. Enhanced contrast (bright tumor center) observed in posthyperthermia DCE-MRI when compared to prehyperthermia shows increased perfusion after gold nanoshell-mediated hyperthermia. Pre- and posthyperthermia contrast uptake estimated from the Region of Interest (ROI) encompassing the tumor core and whole tumor is illustrated in (g) and (h), respectively.
Figures 3G, 3H:
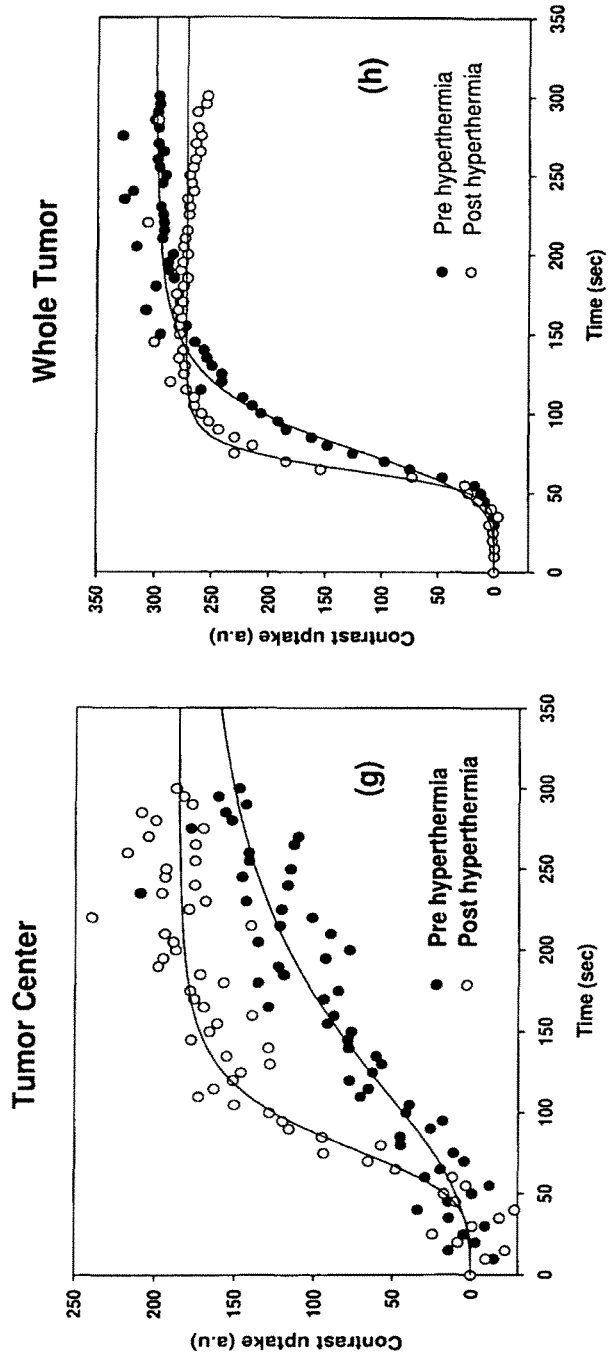

Because one of the purported mechanisms of radiosensitization by mild-temperature hyperthermia is an acute increase in tumor vascular perfusion, dynamic contrast magnetic resonance imaging (DCE-MRI) was used to evaluate contrast uptake in tumors following treatment. Approximately 3-5 min after the completion of laser illumination at standard settings, DCE-MRI was performed in a separate cohort of mice (see supplementary information below for additional details). Representative pre-contrast MRI images and pre- and post-hyperthermia T1-weighted DCE-MRI images are illustrated in FIG. 3-($a$-$c$). The baseline pre-hyperthermia DCE-MRI image (FIG. 3-$b$) revealed contrast enhancement at the periphery of the tumor with relative paucity of contrast in the tumor core. After laser illumination, a significant increase in contrast was observed within the tumor core (FIG. 3-$c$). This increase in contrast within the tumor core is further illustrated by a 3D pixel intensity representation of a region of interest (ROI) (34×37 pixels) encompassing the entire tumor in FIG. 3-($d$-$f$). Pre-hyperthermia contrast-enhanced images demonstrated higher pixel intensity values near the tumor periphery whereas the immediate post-hyperthermia contrast-enhanced images demonstrated an approximately 50% increase in pixel intensity value in the tumor core (FIG. 3-$f$) as compared to the prehyperthermia images (FIG. 3-$e$). The contrast uptake before and after gold nanoshell-mediated hyperthermia in the tumor center and in the whole tumor is further illustrated in FIGS. 3-$g$ & $h$. The slopes (mean±SE) of the pre- and post-hyperthermia contrast uptake in the tumor core were estimated as 2.49±0.51 and 4.38±0.60 arbitrary units (a.u.)/sec, respectively and the corresponding values for the whole tumor were 4.42±0.22 and 8.99±0.69 a.u./sec, respectively.

Ex Vivo Analysis of Tumor Tissue.

Figure 4:
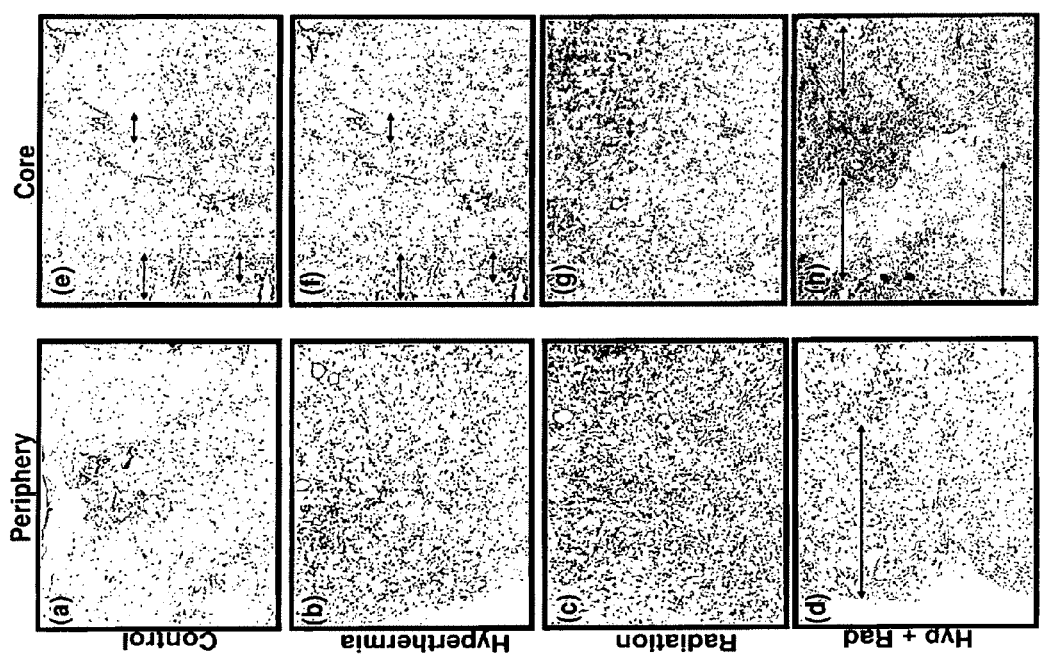
FIGS. 4$a$-$h$ illustrate H and E staining of tumor (a-d) periphery and (e-h) core, tissues from control, hyperthermia, radiation, and thermoradiotherapy treated groups, with the arrows in (e-h) representing the regions of necrosis in the tumor center and the arrow in (d) representing the depth of necrosis from the tumor periphery. A representative scale bar is shown in the bottom image of each column.

Two mice from each group were euthanized 90 min after all treatment and tumors were extracted for ex vivo analyses. Hematoxylin and eosin (H&E) staining of the peripheral and core regions of tumors from all four treatment groups is illustrated in FIG. 4-($a$-$h$) with arrows representing the necrotic regions. No necrotic regions were observed in the tumor periphery of control, hyperthermia and radiation groups (FIG. 4($a$-$c$)), respectively. However, necrotic regions were observed at a distance of ~1.4 mm from the tumor periphery in the thermoradiotherapy group (FIG. 4-$d$). The tumor core of control, hyperthermia and radiation groups demonstrated small necrotic regions in the range of ~0.17-0.4 mm (FIG. 4-($e$-$g$)), respectively. In contrast to these small necrotic regions, large necrotic regions in the range of ~0.6-1.2 mm were observed in the tumor center of the thermoradiotherapy group (FIG. 4-$h$).

Markers for Tissue Hypoxia, Blood Flow and Proliferation.

Figure 5:
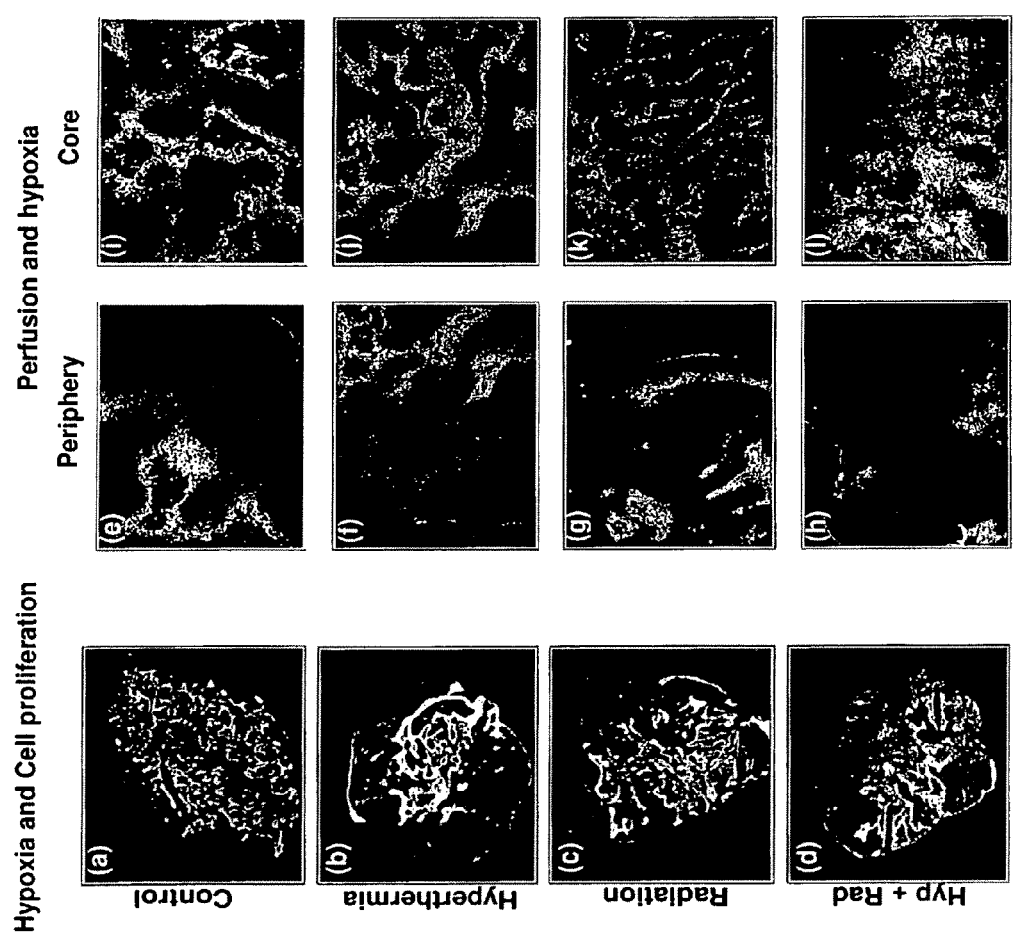
FIGS. 5$a$-$l$ illustrate immunofluorescence staining of control, hyperthermia, radiation, and thermoradiotherapy treated tumors showing hypoxia, cell proliferation (a-d), and hypoxia, perfusion in tumor periphery (e-h), and tumor core (i-l), respectively. The white and grey colors on these images represents cell proliferation, perfusion, and hypoxic regions in tumors. Patchy hypoxic region seen in (l) is attributed to the vascular disruption effect induced by gold nanoshell-mediated thermoradiotherapy. Scale bars are represented in the bottom image of each column.

To further understand the mechanism of extensive necrosis noted on H&E staining, these tumor specimens from all four groups were evaluated for changes in tumor cell proliferation as well as changes in the tumor microenvironment, specifically with assessment of hypoxia and blood flow (see supplementary information below for marker injection and immunofluorescence staining procedure). The hypoxic (white) and proliferative (grey) regions in control, hyperthermia, radiation and thermoradiotherapy groups are represented in FIGS. 5(a-d), respectively. In the control and radiation groups, the hypoxic regions were predominantly in the tumor core while the proliferative regions were largely confined to the periphery of the tumor. However, in the hyperthermia group (FIG. 5-b), the proliferative regions extended to the tumor core with a corresponding decrease in the hypoxic area in the tumor core. This may be attributable to the increased vascular perfusion induced by gold nanoshell-mediated hyperthermia. Higher magnification images of the periphery and tumor core of different treatment groups demonstrating blood perfusion and tissue hypoxia are shown in FIGS. 5-(e-h) & (i-l), respectively. Regions of blood flow (grey) are associated with scant tissue hypoxia (white). At higher magnification, more distinct differences in the patterns of the hypoxic region were observed between the thermoradiotherapy and other groups. The control, hyperthermia and radiation groups demonstrated a structured pattern of a hypoxic region in the tumor core with regions of perfusion between the hypoxic regions (FIG. 5-(i-k)). In contrast to this, the thermoradiotherapy group demonstrated a distortion of this architecture characterized by patchy hypoxic regions with no distinct regions of blood flow in the tumor core (FIG. 5-i). We hypothesized as a reflection of a hindrance to perfusion that also explains the massive necrosis observed on H&E staining.

Assessment of Tumor Microvessels.

Figure 6:
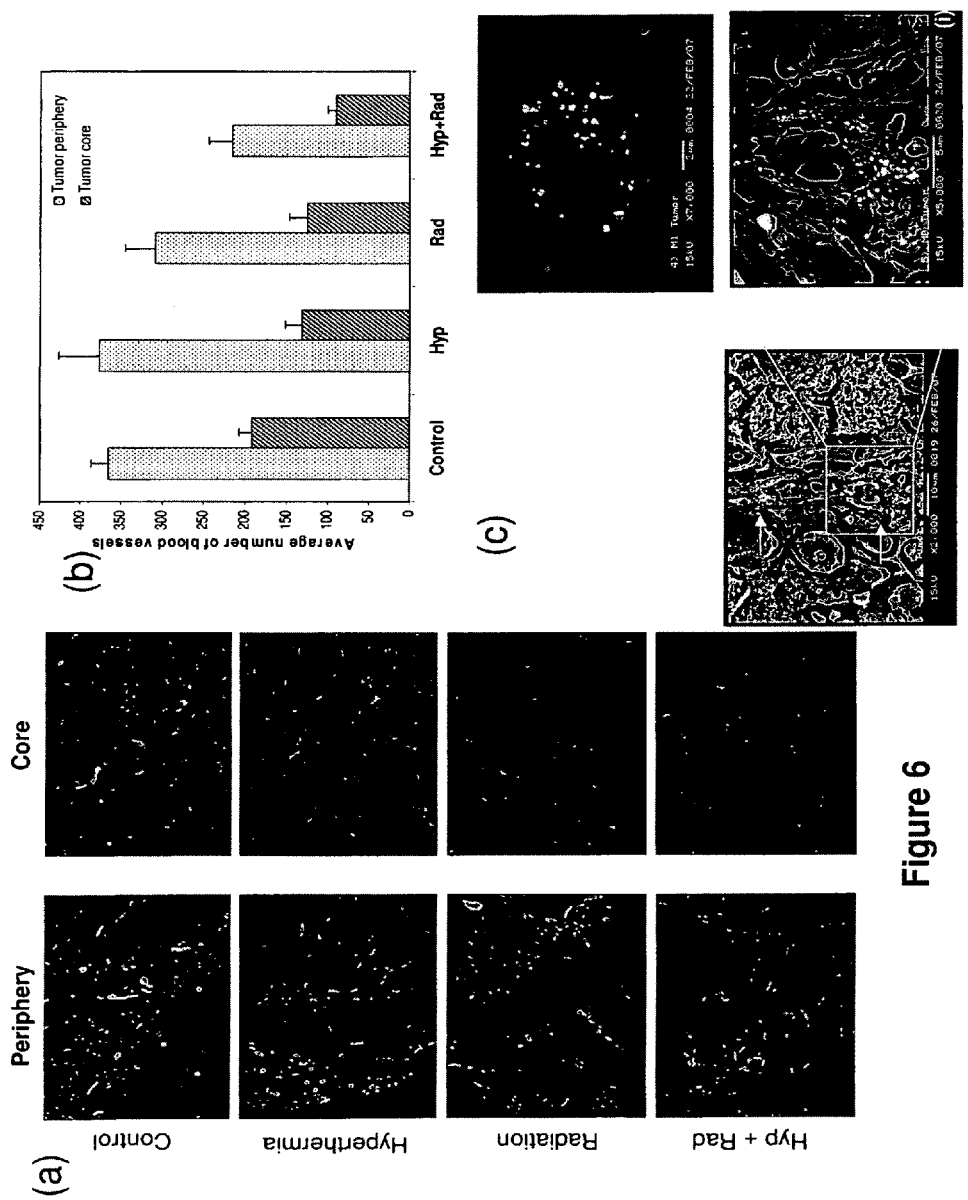
FIGS. 6$a$-$c$ illustrate (a) Immunofluorescence staining for the microvessel density in control, hyperthermia, radiation, and thermoradiotherapy treated tumors showing the vessel distribution in tumor periphery (column 1) and tumor center (column 2). (b) Bar chart representing mean±SE of blood vessels in tumor periphery and tumor core for different treatment groups. (c) SEM images showing the low and high magnification images of gold nanoshell distribution near the perivascular regions in tumors before (row 1: low magnification: 1000×; high magnification: 7000×) and after (row 2: low magnification: 2000×; high magnification: 5000×) gold nanoshell-mediated hyperthermia. The indicating arrows show the gold nanoshell distribution.

To evaluate the pattern of tumor vasculature in all four groups, CD31-immunofluorescence staining was performed on all tumors extracted 90 min following treatments (FIG. 6-a). No significant difference in the microvessel density was observed between the control, hyperthermia and radiation groups. However, the microvessel density was significantly lower ($p<0.05$) in the thermoradiotherapy group compared to other groups. The differences in microvessel density in the tumor periphery and the tumor core of all groups are illustrated in FIG. 6-b, which confirm the relative scarcity of microvessels in tumors treated with thermoradiotherapy. Therefore, these results indicate that thermoradiotherapy leads to an acute increase in perfusion of tumors immediately following hyperthermia (as demonstrated by DCE-MRI 3-5 min following hyperthermia) and a subsequent distortion of vascular patterns (as demonstrated by the decrease in microvessel density 90 min following radiation). These observations are best explained by the nature of hyperthermia induced by gold nanoshells wherein focal temperature rises are much more pronounced adjacent to the nanoshells as compared to further away from them, thereby creating heterogeneity in the distribution of temperature within the entire tumor. Because this heterogeneity, with sharp temperature gradients around the nanoshells, may contribute to the observed vascular pattern disruption, the precise location of gold nanoshells within tumors in the control and hyperthermia groups was determined.

Localization of Gold Nanoshells within the Tumor Microenvironment.

The microscopic distribution of gold nanoshells in tumors was determined by scanning electron microscopy (SEM). SEM was performed using a JSM-5910 scanning electron microscope operating at an accelerating voltage of 15 kV (JEOL, USA, Inc., Peabody, Mass.). In control tumors, SEM images revealed predominant accumulation/distribution of nanoshells in perivascular regions (~50-70 μm from the vascular endothelium, represented by white arrows) in the tumor tissues (FIG. 6c row 1). Similarly, in the hyperthermia group, SEM images (FIG. 6c row 2) revealed intact blood vessels with nanoshells distributed in the perivascular region. Taken together, this perivascular sequestration of gold nanoshells leads to a focal temperature rise near the blood vessels after hyperthermia, which, in turn, leads to (i) an acute increase in perfusion (FIG. 3) and (ii) a greater focal sensitivity to subsequent radiation that results in vascular disruption (FIG. 5-i).

Supplementary Information

MRTI

MRTI was performed using a 1.5 T MR scanner (Signa Echospeed, General Electric Medical Systems, Milwaukee, Wis.) equipped with high performance gradients (23 mT/m maximum amplitude and 120 T/m/sec maximum slew rate) and fast receiver hardware (bandwidth, +/−500 MHz). A receive-only surface coil (3 inch diameter) specially designed for small animal imaging was positioned over the tumor for the MR imaging. T1-weighted (TRITE 600/10.9 Bandwidth 25 KHz NEX 6 FOV 5×2.5 cm matrix 256×192) and T2-weighted (TRITE 4500/15.7 Bandwidth 25 KHz NEX 6 FOV 5×2.5 cm matrix 256×192) images were used to localize the position for the MRTI by verifying the tumor location and the laser axis. MRTI was performed by a complex phase-difference technique (Ishihara, Y.; Calderon, A.; Watanabe, H.; Okamoto, K.; Suzuki, Y.; Kuroda, K.; Suzuki, Y. *Magn Reson Med* 1995, 34, (6), 814-23) with a fast 2-D radiofrequency-spoiled gradient-recalled echo sequence (TR/TE=360 ms/10 ms, flip angle=30°, bandwidth=8.1 kHz; NEX 1; FOV 5×3 cm; matrix 256×128). Real-time temperature was monitored with a fast spoiled gradient-recalled (FSPGR) sequence. Temperature maps and contrast uptake graphs were generated off-line, with the use of MATLAB software (Mathworks, Natick, Mass.).

DCMRI

Dynamic Contrast Magnetic Resonant Imaging was performed using Gd-DTPA (2:5 Gd concentration in saline, 1 μl/gram body weight). An FSPGR sequence was used for the dynamic contrast enhanced (DCE) imaging (TRITE 8.8/2.2 bandwidth 19.2 KHz NEX 12 FOV 5×3 cm matrix 256×128).

Markers Injection

Immediately after each treatment, the animals were injected intravenously with 2.5 mg pimonidazole (Chemicon, Temecula, Calif.) in 0.2 ml sterile saline to target the hypoxic cells. 15 mg of bromodeoxyuridine (Sigma-Aldrich, St. Louis, Mo.) dissolved in 3.0 ml of sterile saline were injected intraperitoneally, 20 and 40 min after the pimonidazole injection. The final injection of 0.4 mg of Hoechst 33342 (Sigma-Aldrich, St. Louis, Mo.) in 0.1 ml of sterile saline was administered intravenously 60 min after pimonidazole injection and 1 min before euthanasia, Animals were euthanized by cervical dislocation and the tumor tissues were immediately dissected exactly into two halves along the central axis of the tumor. One half of the tumor tissue was frozen in dry ice with optimum cutting temperature (OCT) medium and stored at −80° C. and sequential sections of ~6 to 8 μm thickness were made for immunofluorescence staining. The other half of the tumor tissue was divided into two pieces and fixed in formalin for hematoxylin and eosin (H&E) staining.

Immunofluorescence Staining

Three sequential sections from, each animal were used for immunofluorescence staining. Hypoxic cells were stained overnight (at 4° C.) with primary mouse anti-pimonidazole antibody (Chemicon, Temecula, Calif.) diluted (1:50) in antibody diluent (Dakocytomation) followed by 1 hr incubation (at 20° C.) with Alexa 488 ($\lambda_{ex}$=488 nm, $\lambda_{ex}$=520 nm) labeled anti-mouse secondary antibody (Molecular Probes, Eugene, Oreg.) diluted (1:100) in antibody diluent. Proliferating cells were identified by incubating the tissue sections with 2N HCl for 10 min (at 20° C.) for DNA denaturation (Zymed) followed by 10 min incubation with 0.1M Borax (at 20° C.). Sections were incubated overnight (at 4° C.) with biotinylated anti-bromodeoxyuridine antibody (Molecular Probes, Eugene, Oreg.) diluted (1:50) in antibody diluent followed by 1 hr incubation (at 20° C.) with Alexa 568 ($\lambda_{ex}$=568 nm, $\lambda_{ex}$=603 nm) streptavidin conjugate (Molecular Probes, Eugene, Oreg.) diluted (1:200) in antibody diluent. Microvessel staining was performed by overnight incubation (at 4° C.) with 1:200 (diluted in antibody diluent) primary rat monoclonal anti-CD31 antibody (Pharmingen) followed by 1 hr incubation (at 20° C.) with TexasRed ($\lambda_{ex}$=596 nm, $\lambda_{ex}$=615 nm) labeled secondary anti-rat IgG (1:100) (Jackson Scientific) to stain the vasculature. Stained tissues were covered with a cover slip using an anti-fade fluorescence-mounting medium and observed under a Leica DM4000B fluorescence microscope (Leica Microsystems, Wetzlar GmbH, Germany) equipped with a CCD camera (RT KE/SE, Diagnostic Instruments Inc., Sterling Heights, Mich., USA). The fluorescence from the Hoechst, Alexa-488, Alexa-568 and TexasRed were collected using filter cubes with suitable excitation and emission filters. The excitation and emission bandpass-filter combinations of $\lambda_{ex}$-BP360/40 nm, $\lambda_{ex}$-BP 470/40 nm and $\lambda_{ex}$-BP480/40 nm, $\lambda_{ex}$-BP 527/30 nm were used to detect the fluorescence signal from Hoechst and Alexa-488, respectively. A combination of BP515-560 nm excitation bandpass filter and LP590 nm longpass emission filter was used to detect the Fluorescence emission signal from Alexa-568 and TexasRed. The acquired Fluorescence images were processed and analyzed using NIH ImageJ software.

Conclusions Relating to Examples

These examples indicate that hyperthermia mediated by gold nanoparticles uniquely improves the efficacy of radiation therapy by two mechanisms: (a) an early increase in perfusion which reduces the fraction of hypoxic cells that contribute to radiation resistance and (b) a subsequent (~90 min after treatment) induction of vascular disruption/collapse and extensive necrosis that complements radiation-induced cell death. This unique dual effect of gold nanoparticle mediated hyperthermia is a consequence of the focal temperature rise generated adjacent to tumor vasculature where nanoshells have sequestered preferentially. The first mechanism of improvement in the efficacy of radiation therapy observed was due to the increased vascular perfusion of the tumor. Tumors are typically perfused by a network of morphologically and functionally abnormal vessels recruited by an orchestrated series of dynamic events (angiogenesis) driven by the increasing demand for oxygen and nutrients by proliferating tumor cells. Jain, P. K.; Lee, K. S.; El-Sayed, I. H.; El-Sayed, M. A. *J Phys Chem B* 2006, 110, (14), 7238-48; and Jain, R. K. *Cancer Res* 1988, 48, (10), 2641-58. The resulting temporal and spatial heterogeneity of blood flow leads to distinct regions where cells located distal to a functional feeding blood vessel receive insufficient oxygen due to its consumption by the cells closer to the blood vessel. These hypoxic cells maintain their clonogenicity but their sensitivity to radiation is up to three times less than that of normally oxygenated cells. Brown, J. M. *Methods Enzymol* 2007, 435, 295-321. These radioresistant cells not only contribute to tumor progression but also their location distant from blood flow inevitably means that blood-borne therapeutics has limited access to them. Increasing perfusion via gold nanoshell-mediated hyperthermia, therefore, reduces the fraction of cells within a tumor that are hypoxic and thereby enhances radiation sensitivity.

The second mechanism of improvement of efficacy of radiation therapy observed was due to vascular disruption. Vascular disruption has been proposed as a viable anti-tumor strategy because damaging a single established blood vessel, be it via subtle structural changes of dysmorphic endothelial cells or induction of intravascular coagulation, could potentially eliminate hundreds or thousands of tumor cells downstream. Vascular disrupting agents in preclinical and early clinical development include combretastatin A4 phosphate (CA4P), ZD6126, TZT-1027, AVE8062, ABT-751, and MN-029, which target the tubulin cytoskeletal network of endothelial cells; 5,6-dimethylxanthenone-4-acetic acid (DMXAA), which targets autocrine endothelial regulatory cascades; and exherin which targets cell adhesion. Patterson, D. M.; Rustin, G. *J. Clin Oncol* (R Coll Radiol) 2007, 19, (6), 443-56; Hinnen, P.; Eskens, F. A. *Br J Cancer* 2007, 96, (8), 1159-65; Jameson, M. B.; Baguley, B. C.; Kestell, P.; Zhao, L.; Paxton, J. W.; Thompson, P. I.; Waller, S. *Cancer Chemother Pharmacol* 2007, 59, (5), 681-7; O'Hanlon, L. H. *J Natl Cancer Inst* 2005, 97, (17), 1244-5; O'Hanlon, L. H., *J. Nat'l Cancer Inst.* 2005, 97, 17, 1244-45; Tozer, G. M.; Kanthou, C.; Baguley, B. C. *Nat Rev Cancer* 2005, 5, (6), 423-35; Siemann, D. W.; Rojiani, A. M. *Int J Radial Oncol Biol Phys* 2005, 62, (3), 846-53; and Siemann, D. W.; Horsman, M. R. *Expert Rev Anticancer Ther* 2004, 4, (2), 321-7. While these agents have shown promise in early trials, there is concern that more than just tumor vessels may be targeted by systemic exposure to these agents. In particular, damage to vascular compartments outside the tumor may contribute to acute coronary syndromes and thromboembolic events. Van Heeckeren, W. J.; Bhakta, S.; Ortiz, J.; Duerk, J.; Cooney, M. M.; Dowlati, A.; McCrae, K.; Remick, S. C. *J Clin Oncol* 2006, 24, (10), 1485-8; and Van Heeckeren, W. J.; Sanbom, S. L.; Narayan, A.; Cooney, M. M.; McCrae, K. R.; Schmaier, A. H.; Remick, S. C. *Curr Opin Hematol* 2007, 14, (5), 468-80. In contrast to these agents, gold nanoshell-mediated hyperthemia causes vascular disruption that is localized to the tumor, permitting further increase in therapeutic ratio.

The observed radiation dose modification by gold nanoshells is similar to that observed with other forms of hyperthermia. The degree of necrosis observed, however, far exceeds that noted with traditional means of achieving hyperthermia. Notably, this model only evaluates the effects of this combination on single-fraction high dose radiation therapy, similar to that used in clinical stereotactic radiation therapy applications. This therapeutic challenge could be converted to an opportunity for targeted therapy using drugs targeting the hypoxia-inducible factor-1 transcription factor, prodrugs activated by hypoxia, hypoxia-specific gene therapy, and recombinant anaerobic bacteria. Alternate sequencing strategies and alterations of the degree of temporal separation between hyperthermia and radiation may be employed to maximize the likelihood that radiation is administered during periods of peak radiosensitivity defined by an optimal tumor oxygenation window or a vascular normalization window. Dings, R. P.; Loren, M.; Heun, H.; McNiel, E.; Griffioen, A. W.; Mayo, K. H.; Griffin, R. *J. Clin Cancer Res* 2007, 13, (11), 3395-402; and Winkler, F.; Kozin, S. V.; Tong, R. T.; Chae, S. S.; Booth, M. F.; Garkavtsev, I.; Xu, L.; Hicklin, D. J.; Fukumura, D.; di Tomaso, E.; Munn, L. L.; Jain, R. K. *Cancer Cell* 2004, 6, (6), 553-63. Lastly, targeting gold nanoshells to tumor vasculature may further localize and concentrate nanoshells along tumor vasculature to facilitate tumor-directed therapy beyond image-guided physical collimation of the laser beam to the tumor alone. Additional clinical benefit could be realized if substances with a high atomic number (Z) accumulate in tissues leading to greater radiation dose deposition, particularly while utilizing kilovolt radiation therapy where highly Z-dependent photoelectric interactions are the predominant form of interaction. However, preliminary calculations, Monte Carlo estimations and in vitro experiments do not bear this out to be a sufficient source of dose escalation to be clinically significant (data not shown). This is likely due to the insufficient tumor parenchymal penetration beyond the immediate perivascular space by the 160 nm nanoshells and the relatively low gold content of each nanoshell in contrast to the significant dose enhancement achievable with smaller nanogold particles. Hainfeld, J. F.; Slatkin, D. N.; Smilowitz, H. M. *Phys Med Biol* 2004, 49, (18), N309-15.

While the examples illustrate the use of gold nanoshells to transducer near-infrared light, there are numerous other examples of nanoparticles that may be used to transducer this or other energy. See e.g., Liu Z, Cai W, He L, Nakayama N, Chen K, Sun X, Chen X, Dai H "In vivo biodistribution and highly efficient tumour targeting of carbon nanotubes in mice," *Nat Nanotechnol.* 2007 January; 2(1):47-52; Gannon C J, Patra C R, Bhattacharya R, Mukherjee P, Curley S A. "Intracellular gold nanoparticles enhance non-invasive radiofrequency thermal destruction of human gastrointestinal cancer cells." *J Nanobiotechnology,* 2008 Jan. 30; 6:2. Additionally, while the examples describe the passive accumulation of nanoparticles in the tumor, one of ordinary skill will recognize that the nanoparticles may be actively targeted to cell surfaces. See e.g., Lowery A R, Gobin A M, Day E S, Halas N J, West J L., "Immunonanoshells for targeted photothermal ablation of tumor cells," *Int J Nanomedicine,* 2006, 1(2), 149-54.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method for the treatment of a tumor residing in a target area of an organism comprising:
    introducing a plurality of nanoparticles into a circulating blood of an organism;
    allowing the nanoparticles to preferentially accumulate in the target area;
    applying an external energy to the target area wherein the nanoparticles are adapted to transduce at least a portion of the external energy into heat energy, wherein the external energy is electromagnetic energy;
    wherein the electromagnetic energy is selected from the group consisting of ultraviolet light, visible light, infrared light, microwaves, and a combination thereof;
    wherein the heat energy causes a rise in temperature in the target area;
    allowing the temperature of the target area to elevate to a localized elevated temperature by way of a transduction of the external energy into heat energy by the nanoparticles, wherein the localized elevated temperature is non-ablative, wherein the localized elevated temperature increases perfusion and/or reduces hypoxia of the tumor; and
    applying ionizing radiation to the target area at a time during the increased perfusion and/or the reduced hypoxia.

2. The method of claim 1 wherein the ionizing radiation disrupts the cells in the area of the localized elevated temperature.

3. The method of claim 2 wherein the method increases a hypoxia of the tumor.

4. The method of claim 3 further comprising introducing a hypoxia-targeted therapy to the tumor.

5. The method of claim 4 wherein the hypoxia-targeted therapy comprises an anerobic bacterial spore.

6. The method of claim 4 wherein the hypoxia-targeted therapy is an inhibitor of H1F1 Alpha or thioredoxin.

7. The method of claim 1 wherein the nanoparticles are selected from the group consisting of: nanoshells, nanorods, carbon nanotubes, fullerenes, carbon fullerenes, metallic nanoparticles, metal colloids, carbon particles, buckyballs, nanocubes, nanostars, indocyanine green encapsulated in nanoparticles, acoustic particles, and any combination thereof.

8. The method of claim 1 wherein the nanoparticles comprise any particle suitable for transducing electromagnetic energy into heat energy.

9. The method of claim 4 wherein the step of introducing the hypoxia-targeted therapy to the tumor comprises systemically introducing the hypoxia-targeted therapy into the circulating blood of the organism.

10. The method of claim 1 further comprising introducing a therapeutic agent to the tumor.

11. The method of claim 10 wherein the therapeutic agent comprises a chemotherapeutic drug.

12. The method of claim 10 wherein the therapeutic agent comprises a gene therapy vector.

13. The method of claim 10 wherein the therapeutic agent comprises a drug delivery vector.

14. The method of claim 13 wherein the drug delivery vector is selected from the group consisting of: liposomes, micelles, hollow nanoparticles, drug eluting nanoparticles, and any combination thereof.

15. The method of claim 10 wherein the therapeutic agent comprises an immunotherapeutic agent.

16. The method of claim 10 wherein the therapeutic agent comprises vascular targeted therapy.

17. The method of claim 10 wherein the step of introducing the therapeutic agent to the tumor comprises systemically introducing the therapeutic agent into the circulating blood of the organism.

18. The method of claim 1 wherein the accumulation of nanoparticles in the target area results from an enhanced permeability and retention (EPR) effect.

19. The method of claim 1 wherein the accumulation of nanoparticles in the target area results from a ligand conjugated to the nanoparticle that actively targets the vasculature of the tumor.

20. The method of claim 1 wherein the nanoparticles are conjugated with a ligand that actively targets at least a portion of the cells of the tumor so as to result in the accumulation of nanoparticles in the target area.

21. The method of claim 1 wherein the external energy is near infrared light.

22. The method of claim 21 wherein the nanoparticles are selected from the group consisting of: gold nanoshells, gold nanorods, and any combination thereof.

* * * * *